United States Patent [19]

Wiertzfeld et al.

[11] Patent Number: 4,870,968
[45] Date of Patent: Oct. 3, 1989

[54] SYSTEM AND METHOD FOR CONTROLLING THE STIMULATION FREQUENCY OF HEART PACEMAKERS

[75] Inventors: Alexander Wiertzfeld, Thanning; Roland Heinze, Ottobrunn, both of Fed. Rep. of Germany

[73] Assignee: Siemens Aktiengesellschaft, Berlin and Munich, Fed. Rep. of Germany

[21] Appl. No.: 33,883

[22] Filed: Apr. 2, 1987

Related U.S. Application Data

[63] Continuation of Ser. No. 746,738, Jun. 20, 1985, abandoned.

[30] Foreign Application Priority Data

Jun. 20, 1984 [DE] Fed. Rep. of Germany ....... 3422913

[51] Int. Cl.$^4$ .............................................. A61N 1/36
[52] U.S. Cl. ............................................... 128/419 PG
[58] Field of Search ................................ 128/419 PG

[56] References Cited

U.S. PATENT DOCUMENTS

| | | | |
|---|---|---|---|
| 4,009,721 | 3/1977 | Alcidi | 128/419 PG |
| 4,201,219 | 5/1980 | Bozal-Gonzalec | 128/419 PG |
| 4,202,339 | 5/1980 | Wirtzfeld et al. | 128/419 PG |
| 4,399,820 | 8/1983 | Wirtzfeld et al. | 128/419 PG |
| 4,467,807 | 8/1984 | Bornzin | 128/419 PG |
| 4,527,568 | 7/1985 | Rickards | 128/419 PG |

FOREIGN PATENT DOCUMENTS 0059868  2/1982  European Pat. Off.
2717659 10/1978 Fed. Rep. of Germany.

Primary Examiner—William E. Kamm
Attorney, Agent, or Firm—Hill, Van Santen, Steadman & Simpson

[57] ABSTRACT

A follower control matches the stimulation frequency of a heart pacemaker to patient load condition by obtaining measurement values $S_{O2}$ corresponding to the central venous blood oxygen saturation in the heart according to the principle of reflection oximetry, by forming control values $B_{S1}$ according to the quotient $\Delta S_{O2}/\Delta S_{O2max}$ where the numerator is the difference between the current measurement value and a stored reference value (e.g. $S_{O2max}$ or $S_{O2min}$) and the denominator serves to standardize the control value based on the maximum change of the measurement value over a relatively long time interval, and by changing the stimulation frequency by an amount dependent on the magnitude of the control value. Preferably, the stimulation frequency $f_p$ is set directly as a function of the control value $B_{S1}$ and most preferably according to the function $$f_p = f_{min} + \Delta f_{max} e^{-c_w B_{S1}^2} + \Delta f_{opt}$$

where $f_{min}$ is a prescribed minimum frequency, $\Delta f_{max}$ is the maximum frequency difference, $c_w$ is a programmable constant and $\Delta f_{opt}$ is a frequency change introduced by a concurrently operating optimizing control. Artifacts are avoided by obtaining measurement values at sampling intervals distributed in the time span between heart beats and varying in phase during each measurement cycle, and then selecting the minimum measurement value occurring in each measurement cycle.

16 Claims, 4 Drawing Sheets

SYSTEM AND METHOD FOR CONTROLLING THE STIMULATION FREQUENCY OF HEART PACEMAKERS

This is a continuation of application Ser. No. 746,738, filed June 20, 1985, now abandoned.

BACKGROUND OF THE INVENTION

The invention relates to a control system and method for matching the stimulation frequency of a heat pacemaker to the varying load condition of a patient.

In a control system such as disclosed for example in U.S. Pat. No. 4,399,820 issued Aug. 23, 1983, a measurable variable $S_{O2}$ corresponding to the central venous blood oxygen saturation in the heart is identified according to the principle of reflection oximetry, and a controlled variable is derived therefrom in that changes of this measurable variable over a given time increment are standardized to the maximum change of the measurable variable over long time intervals such as hours or days.

In a control system of this type, there is further provided a processing means for storing the measurable variable $S_{O2}$ as ascertained in successive short time intervals, and also storing limit values $S_{O2max}$ and $S_{O2min}$ which are respectively the maximum and minimum values of the measurable variable as ascertained over a relatively long time interval. From these maximum and minimum values, a maximum change of the measurable variable is obtained, which may be designated by the notation $\Delta S_{O2max}$. A first controlled variable is then obtained by forming the quotient of a change in the measurable variable, designated $\Delta S_{O2}$, and the maximum change $\Delta S_{O2max}$. In this way, the change in the measurable variable over a short time interval is standardized on the basis of the maximum change of the measurable variable over a relatively long time interval.

A long-term, undisturbed measured value acquisition and a good haemodynamic situation in the blood circulation are already obtainable with the control system of U.S. Pat. No. 4,399,820. In this system, so called follower control is effected such that the frequency is modified by a constant amount $\Delta f$ whenever the controlled variable exceeds a prescribable value. In the control system of the U.S. patent, an optimizing control is superimposed on the follower control, the optimizing control becoming effective when no frequency modification has been produced by the follower control over a prescribable time interval.

The known control system uses chronological changes of the standardized measurable variable as control signal. The consequence of this is that the frequency changes are time-dependent and the stimulation frequency changes dependent on the duration of the change in the blood oxygen saturation. Identical overall changes of the blood oxygen saturation can therefore lead to different changes of the heart frequency depending on how quickly they occur. In unfavorable cases, this type of follower control can lead to the result that the follower control does not achieve values that are physiologically optimally matched. These non-optimum control values are then not compensated until the subsequent optimizing control. Under certain conditions, however, this type of successive follower and optimizing control can lead to unstable conditions, whereby the heart rate oscillates between the prescribed limit values as a consequence of periodically fluctuating load conditions. It has also been shown that the chronological separation of the two control events, i.e. the separation of the follower control and of the optimizing control by a substantial intervening time interval, can prevent optimizing of the control action when short-duration changes of the blood oxygen saturation are present which are superimposed on a steady state and elicit a frequency change via the follower control.

In addition to this control method of U.S. Pat. No. 4,399,820, wherein chronological changes of the measurable variable are used as controlled variable, U. S. Pat. No. 4,202,339 discloses a method wherein the frequency matching of the heart pacemaker is effected according to the relationship $$f_p = k \cdot S_{O2}, \quad f_{min} < f_p < f_{max}$$

that is wherein the heart pacemaker frequency $f_p$ is varied according to the respectively identified measured value of the blood oxygen saturation itself. The values for k, $f_{min}$ and $f_{max}$ are in this case permanently selected before the implantation. This control method exhibits a number of problems: Thus, no changes can be allowed to appear on the optical transmission link. Deposits on the measuring probe or foreign objects in the reflection region (cardiac wall, trabecula) also lead to falsifications of the measured results. Further, this control principle requires a calibration before implantation. A considerable improvement of this situation could already be achieved if a programmable heart pacemaker which could also supply intracardial measurable variables to an external monitoring and control station in dialogue were employed. A new calibration and, thus, a new determination of the characteristic could thus be undertaken under given conditions at regular intervals or as needed. The outlay required therefor, however, is undesirably high.

SUMMARY OF THE INVENTION

A principal object of the invention is to match the heart rate to respective patient load conditions even better and faster, whereby the optimum haemodynamic situation is maintained by the heart pacemaker itself even over long time spans independently of disturbing influences of the system such as partial coating of the measuring probe or deterioration of the properties of the opto-electronic elements.

A further goal of the invention is to suppress disturbing influences in the acquisition of the measurable variable corresponding to the central venous blood oxygen saturation even better than heretofore.

A major improvement is achieved by utilizing the basic control strategy of generating a standardized controlled variable, but instead of introducing frequency changes in fixed increments, carrying out follower control by means of frequency changes of respective magnitudes which are functions of the respective values of the standardized controlled variable.

Further improvements are achieved by various preferred developments of the invention as hereafter described and claimed.

The time-dependency of the follower control has been eliminated by the control system of the present invention. Further, chronological changes of the measurable variable can be employed as controlled variable. The frequency changes thereby generated are, however, dependent on the magnitude of the controlled variable. Rapid changes in the blood oxygen saturation thus generate greater frequency discontinuities than slow changes. Even as a result of this, the heart rate is matched to the respective load conditions better than previously.

In a further development of the invention, the controlled variable is based on a differential between a measured variable and a fixed value, in addition to being standardized. The differences between successive measured values are no longer employed as in U.S. Patent 4,399,820; instead control values are used which are based on the difference between respective measured values and the maximum or minimum measured value, $S_{O2max}$ or, respectively, $S_{O2min}$. Thereby achieved is that the controlled variable $B_{S1}$ that is formed contains information about the range of the overall oxygen measuring scope in which the momentary measured value is situated. Expressed in other words, this means that information concerning the prevailing relative degree of physical load is contained in the controlled variable formed in this fashion.

An even more rapid matching of the heart rate to load conditions can be achieved in accordance with the invention when it is no longer a frequency change that is defined as a function of the controlled variable but the heart rate that is directly defined as a function of this controlled variable. This, in turn, corresponds to a type of characteristic control, but no longer with a rigidly prescribed characteristic as in the prior art, but rather with a standardized characteristic which prescribes the manner in which the rate of the heart pacemaker is matched to the conditions as determined by the control system. Investigations have shown, for example, that the maximum fluctuations in blood oxygen saturation can vary greatly over the course of longer time spans (weeks, months). This fluctuation scope decreases over the course of time and, further, the absolute position of the fluctuation range also shifts. The characteristic of the preferred control system can produce heart rates applicable to the entire range between minimum and maximum blood oxygen saturation but the control system will not produce frequencies beyond the range of such applicable heart rates. That is simply and automatically assured by the inventive standardization.

A linear characteristic will be selected in the simplest case. Again, however, investigations have shown that the required frequency changes given high load, i.e. minimum blood oxygen saturation, must already be rather high for the case of a slight change in the blood oxygen saturation but that smaller changes in the oxygen saturation should have hardly any influence on the frequency in the quiescent condition, i.e. given maximum blood oxygen saturation. Provided on the basis of these investigations in a further development of the invention for the improvement of the haemodynamic situation is that the control operates according to the function:

$$f_p = f_{min} + \Delta f_{max} \, e^{-c_w} \cdot \left( \frac{S_{O2} - S_{O2min}}{S_{O2max} - S_{O2min}} \right)^2 + \Delta f_{opt}$$

The prescribable minimum frequency is referenced $f_{min}$ and the maximum frequency change is referenced $\Delta f_{max}$. The term $c_w$ is constant and $\Delta f_{opt}$ is an additional frequency change due to an optimizing control. The optimizing control is provided simultaneously, in addition to the characteristic control with a standardized, adapted characteristic and not in chronological succession as in the prior art. Characteristic regulation and optimizing regulation act continuously in juxtaposition, whereby, in the former instance, a specific function is allocated to every value of blood oxygen saturation and, for the optimizing regulation, the tendency of the value of blood oxygen saturation is continuously monitored and a determination is made as to whether an improvement (boost in measured value) of the value of blood oxygen saturation results from an independent raising and lowering of the frequency by the frequency difference $\Delta f_{opt}$.

It is no longer a specific characteristic but an entire family of characteristics that is now allocated to every value of blood oxygen saturation. The upper and lower limits are fixed by the maximally allowed optimizing control. Since the measuring sensitivity of the control system also decreases with a decreasing maximum scope of blood oxygen saturation fluctuation, it is provided in a preferred development of the invention that, when the measuring precision falls below a prescribable, first value, the optimizing control is interrupted and, given a further drop below a second value, the follower control is also interrupted. A simple factor is thus created which allows the patient himself to determine when the control system enters into a critical phase and a replacement is required under given conditions or at least a checkup by the physician.

Since, given unaltered load condition, the optimizing control experimentally undertakes a frequency change after a certain time span, it is sufficient that the patient have been at rest for a while and then determines by taking his pulse whether a frequency discontinuity appears or not. When he does not detect an elevation in frequency, then the optimizing control is out of operation.

In order to compensate for disturbances in the measured signal acquisition, the prior art as disclosed in U.S. Pat. No. 4,399,820 provides that the mean value of the measured signals be formed via an integrator over a prescribed time span. As investigations, however, have surprisingly shown, considerable artifacts which lie correlated to the heartbeats can be superimposed on the measurable variables. Under unfavorable conditions, the known mean value formation can thus lead to considerable falsifications of the measured signal. It is therefore provided in a further development of the invention that the minimum value of the signal of the sensor occurring in a given measurement interval is employed as the measured variable $S_{O2}$. This minimum value corresponds to the lowest blood oxygen saturation and is thus best representative of the load condition during such measurement interval. The artifacts can, for example, appear in that the measuring probe is moved due to the contraction of the heart and, for example, proceeds into the proximity of the cardiac wall, whereby the reflection and, thus, the measured signal are increased.

Only following this minimum value formation is it meaningful to also undertake a mean value formation. Since, as has been shown, the artifact do not lie stochastically distributed but are practically chronologically fixed in the interval between the heartbeats and since the measurable variable is identified only during sampling intervals that are very short in comparison to the chronological spacing of two heartbeats, it is provided, in order to avoid the use of measurement values influenced by such artifacts that the chronological position of the sampling intervals is variable. The entire range between the heartbeats can thus be scanned at least over the course of several heartbeats.

It is also possible for a faster avoidance of the influence of artifacts to distribute a plurality of sampling intervals over the time span between two heartbeats. A solution that is technically particularly advantageous results when a larger number of potential sampling intervals is permanently distributed over the time span between two heartbeats, but that only a few of these sampling intervals are respectively exploited when it is feasible to save energy in this way and that different sampling intervals from among the potential intervals are used from heartbeat to heartbeat, so that there is practically a phase shift of the sampling intervals employed. Due to the differing dependency of the heartbeat rate on the change of the load condition, it can be advantageous to increase the number of sampling intervals employed per measurement interval with an increasing heart rate.

An illustrative embodiment of the invention shall be described and explained in greater detail below with reference to the figures on the accompanying drawing sheets; and other objects, features and advantages will be apparent from this detailed disclosure and from the appended claims.

DETAILED DESCRIPTION

Figure 1:
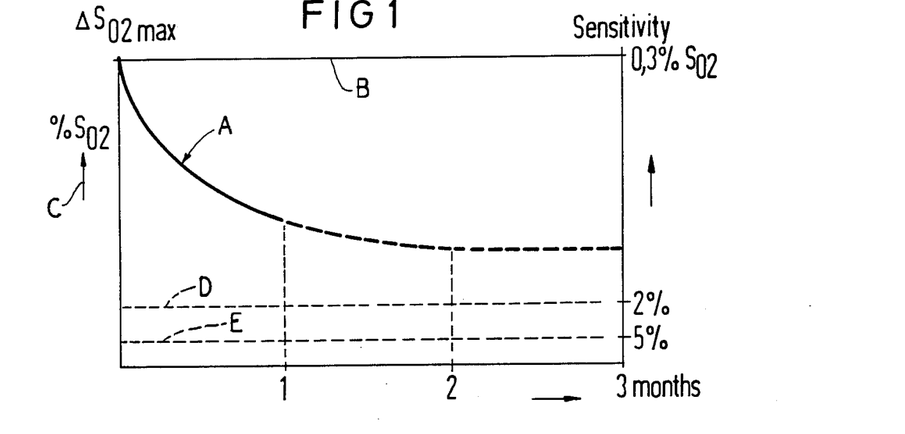
FIG. 1 shows a curve illustrating the variation of maximum fluctuation in blood oxygen saturation as a function of time.

In FIG. 1, a curve A represents the variation in the maximum range of blood oxygen saturation as a function time (measured in months). The line B represents an initial value of the range, designated $\Delta S_{O2max}$ which is taken to represent a one hundred percent reference level. Thus the arrow C at the left in FIG. 1 represents increasing percentage values. Curve A in relation to the left hand ordinate scale thus shows the progressive decrease in percentage value as a function of time. At the right side of FIG. 1, a second ordinate axis is calibrated in terms of sensitivity, i.e. measuring precision. Thus reference level B corresponds with a measurement sensitivity of 0.3 percent, while reference levels D and E correspond with progressively decreased sensitivity values of two percent and five percent, respectively. The empirical curve of FIG. 1 clearly shows that the maximum fluctuation range of the blood oxygen saturation decreases as viewed over longer time spans. Together with this decrease, the measuring precision is also reduced at the same time, this lying at a few tenths of a percent of blood oxygen saturation, for instance, at the beginning. By way of example, two limit values for the sensitivity are indicated by the dash lines D and E. When the maximum fluctuation range of the blood oxygen saturation $\Delta S_{O2max}$ drops below the first limit of two percent measuring precision, then it can be provided that the optimizing control is disabled. Given downward transgression of the lower limit of five percent the follower control is also interrupted.

It can again be clearly derived from the diagram of FIG. 1 that a characteristic control with a rigidly prescribed, invariable characteristic which is supposed to respectively cover the entire fluctuation range of the blood oxygen saturation in terms of frequency is not suitable for long-term control due to this great variation in the fluctuation range.

Figure 2:
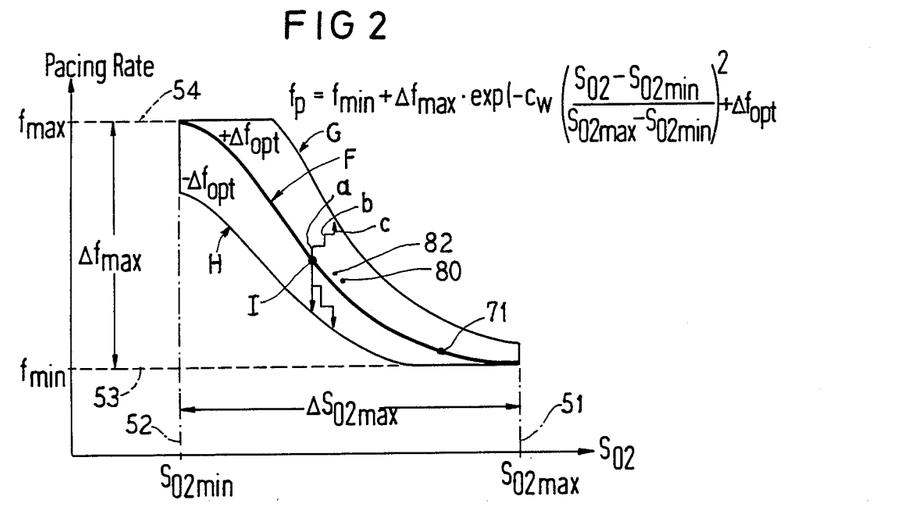
FIG. 2 shows a preferred control characteristic in accordance with the present invention wherein the stimulation frequency is selected based on a non-linear function of a controlled variable which controlled variable is derived from measured values of blood oxygen saturation.
Figure 3:
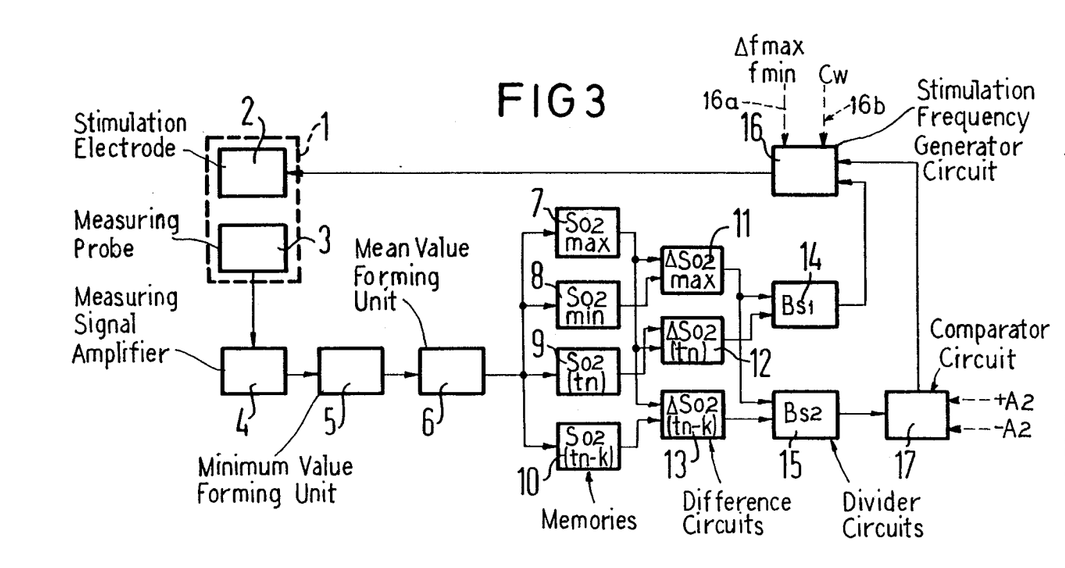
FIG. 3 is a block diagram illustrating a preferred heart pacemaker control system in accordance with the present invention.

In the diagram of FIG. 2, curve F represents the heart pacemaker frequency (pacing rate) which is to be established by the preferred control system of FIG. 3 for respective measured values of blood oxygen saturation $S_{O2}$. The curve F shows a non-linear preferred characteristic corresponding to the mathematical expression also given in FIG. 2 (at the upper right). Tests have shown that an optimum matching of the heart rate to the respective load conditions is achieved with this function. To effect this control function the minimum frequency $f_{min}$ and the maximum frequency change $\Delta f_{max}$ allowed are defined in the control system. The function is composed of a fixed value for the minimum frequency, of an exponential term, which contains the product of an adjustable value, particularly a programmable constant, $c_w$ and the square of the controlled variable $B_{S1}$, as well as an additive term $\Delta f_{opt}$. The latter represents the frequency change from that corresponding to curve F due to the optimizing control. The control characteristic of FIG. 2 differs from the known control characteristic of U.S. Pat. No. 4,399,820 in a number of aspects. Thus, a constant characteristic is not employed, rather a standardized characteristic as shown at F is utilized which always automatically adapts the pace rate to the changes sensed by the control system. Further, the optimizing control is executed simultaneously with the follower control via the characteristic of FIG. 2, so that a family of characteristics practically results, these lying in the region defined by the envelopes G and H ($+\Delta f_{opt}$ and $-\Delta f_{opt}$). As an example a control point I is indicated in about the center of the characteristic curve F of FIG. 2. When the measured blood oxygen saturation corresponds to this point I, then the corresponding frequency $f_p$ according to the center or means characteristic F is first established. If the optimizing control indicated by the steps a, b and c in the direction of increasing stimulation frequency leads to an improved blood oxygen saturation, then the frequency variation undertaken in the optimizing control is retained in a fashion known per se. When a subsequent change of the load occurs, the frequency followup results according to a characteristic shifted by this $\Delta f_{opt}$ from the base curve F.

The most important functions of the pacemaker of the invention are shown in a block diagram in FIG. 3. Both the stimulation electrode 2 and the measuring probe 3 are shown as being contained in the block 1 shown with dash lines and representing the catheter system. The signal of the measuring probe 3 is supplied to a measuring amplifier 4 and proceeds from there to a minimum value forming unit 5 which shall be explained later with reference to FIG. 5. The output signal of the minimum value forming unit proceeds via a mean value forming unit 6 to four memories 7 through 10 in parallel, whereby the memory 7, for example, stores the maximum value of the blood oxygen saturation and the memory 8 stores the minimum value of the blood oxygen saturation. The memory 9 contains the signal value for the current measuring time $t_n$ and the memory 10 contains the earlier signal value from a measuring time $t_{n-k}$.

Figure 6:
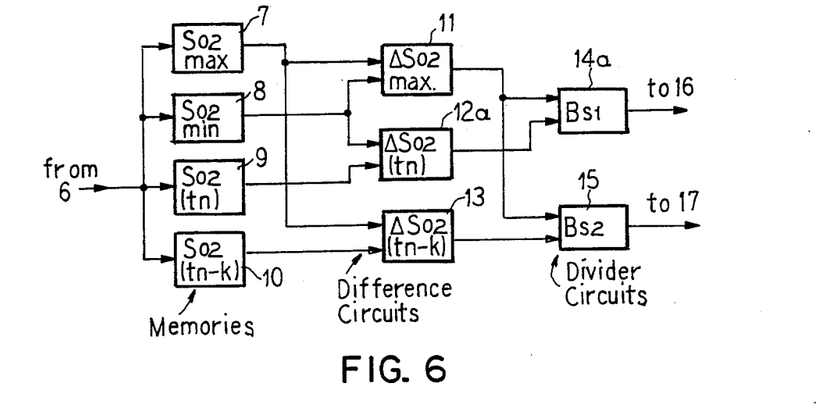
FIG. 6 is a block diagram of a portion of a system of FIG. 1 showing another embodiment of the memories, divider circuits and difference circuits.

The memories are followed by three difference forming units 11 through 13. The measured value difference $\Delta S_{O2max}$ between the maximum blood oxygen saturation value acquired over a longer time span and stored in the memory 7 and the minimum blood oxygen saturation value correspondingly stored in the memory 8 is formed in the difference forming unit 11. The difference between the new measured value signal existing in the memory 9 at time $t_n$ and the maximum value of the blood oxygen saturation from the memory 7 is formed in the difference forming unit 12. As shown in FIG. 6 the difference between the minimum blood oxygen saturation value present in the memory 8 and the new measured value residing in the memory 9 can likewise be formed in a difference forming unit 12a. The difference between the values of the memories 7 and 10 is correspondingly formed in the difference forming unit 13. The standardized controlled variables $B_{S1}$ and $B_{S2}$ are respectively formed from the values of the difference forming units in the following dividers 14 and 15 in the embodiment of FIG. 3, or the dividers 14a and 15 in the embodiment of FIG. 6.

The value $B_{S1}$ is forwarded directly to a stimulation pulse generator 16 which defines a heart pacemaker rate (frequency) dependent on this value in accord, for example, with the first two terms of the mathematical function indicated in FIG. 2 (curve F, FIG. 2). Simultaneously, the value $B_{S2}$ is forwarded to a comparator 17 which compares the value of the divider 15 to prescribable, particularly programmable fixed values $+A_2$ and $-A_2$ in a fashion know per se from U.S. Pat. No. 4,339,820, and, given upward or, respectively, downward transgression of these values, likewise emits a signal to the stimulation pulse generator 16 which leads to a frequency discontinuity by a constant differential frequency value. The stimulation electrode 2 is driven via the output signal of the stimulation pulse generator 16.

Figure 4:
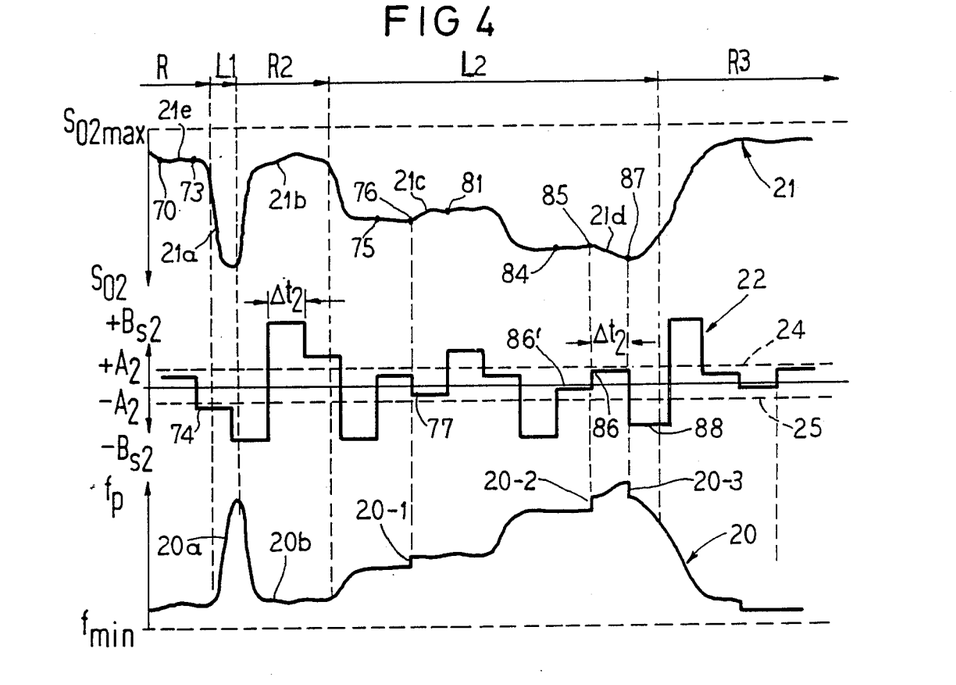
FIG. 4 is a composite diagram illustrating an exemplary variation in a measured variable as obtained by the measurement means of FIG. 3, and showing the control action of the control system of FIG. 3 in response to the course of the measured variable.

The following FIG. 4 shows a curve 20 representing the control of the heart pacemaker stimulation frequency $f_p$ with the assistance of the preferred control system of FIG. 3 as a function of the load of the patient, shown by the relationship to the chronological curve 21 of the measured value of the blood oxygen saturation $S_{O2}$. Curve 22 shows the change in the measured value $B_{S2}$ per time unit $\Delta t_2$, the change of the frequency $f_p$ thereby effected being indicated by abrupt steps such as 20-1, 20-2, and 20-3, of curve 20. Alternately occurring phases of rest and of load are identified in the upper part of FIG. 4 with the designations R1, R2, R3 and L1, L2, respectively. The blood oxygen saturation is entered therebelow by means of curve 21. The curve 22 representing the controlled variable $B_{S2}$ for optimizing control is shown in the middle part of FIG. 4, and the two fixed values $+A_2$ and $-A_2$ are represented by dash lines 24 and 25. The curve 20 of the heart rate $f_p$ is entered in the lower part of FIG. 4. As can be clearly derived from this illustration, the central venous oxygen saturation $S_{O2}$ decreases rapidly at 21a at the beginning of the first load pulse L1. The heart rate $f_p$, however, follows it nearly without delay as shown at 20a. This is achieved by the follower control of FIG. 3 operating according to the standardized characteristic F, FIG. 2 with superimposed optimizing control. In the rest phases following thereupon, the oxygen saturation therefore quickly returns to a far higher value (e.g. as at 21b) which is associated with a nearly simultaneous, corresponding lowering of the heart pacemaker rate (e.g. as shown at 20b).

In the second, far longer load phase that has been shown at L2 in FIG. 4 wherein the oxygen saturation value first assumes an approximately constant value, a small frequency elevation in the heart pacemaker frequency occurs at 20-1 due to the optimizing control. This, as can be appreciated from region 21c of curve 21 representing the blood oxygen saturation, leads to an improved blood oxygen saturation shortly after the frequency change 20-1. This frequency change is therefore retained. In the final region of this load phase L2, an optimizing frequency change is again undertaken, this again being documented in the frequency discontinuity at 20-2 in the lower curve 20 of FIG. 4. This time, however, no improvement of the blood oxygen saturation follows. Instead a rising load follows the frequency change immediately (i.e. the decreasing blood oxygen saturation at 21d). At the end of the time interval $\Delta t_2$ corresponding to region 21d of curve 21, the frequency change due to the optimizing control at 20-2 is cancelled (i.e. at 20-3).

Figure 5:
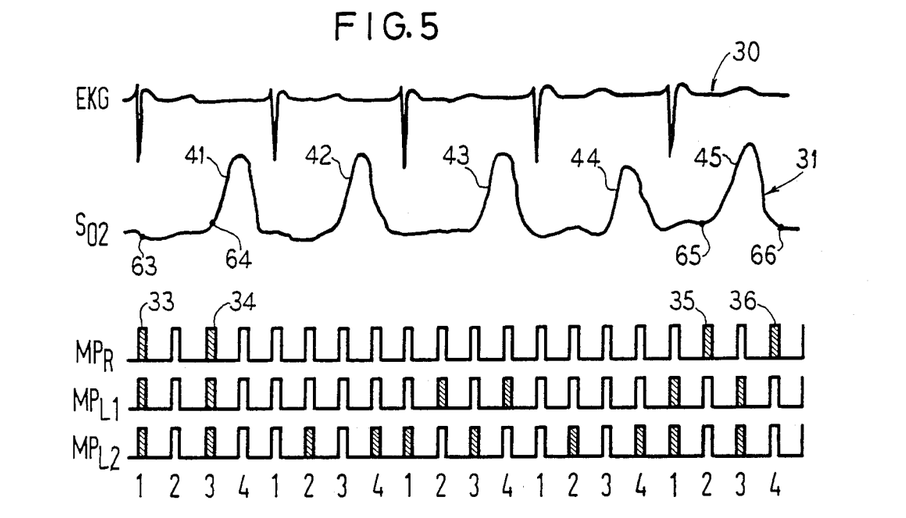
FIG. 5 is a composite diagram illustrating an exemplary electrocardiograph waveform of a patient, and showing an exemplary variation of the blood oxygen saturation as measured by the measuring probe of FIG. 3, FIG. 5 also showing preferred sampling patterns for obtaining the measured variable in the control system of FIG. 3 for different levels of patient load.

An EKG is shown by curve 30 in the upper part of FIG. 5. The curve 31 representing the measurable variable of the blood oxygen saturation $S_{O2}$ is shown below on the same time axis as curve 30. The measuring points at which the blood oxygen saturation is respectively determined for the control system of FIG. 3 during the course of the EKG is shown in the lower part of this FIG. 5. The measuring points of the sequence $MP_R$ are shown by cross hatching at 33, 34 and 35, 36 and represent the preferred sampling points during a resting condition of the patient. The sequence $MP_{L1}$ shows a preferred sampling pattern for a first moderate load condition, while the sequence $MP_{L2}$ shows a preferred sampling pattern for a second, higher load condition. In the sequences of FIG. 5, there are four potential sampling points in each EKG cycle, but not all measuring points are exploited so that energy can be saved. As may be clearly seen in the middle part of FIG. 5 in the illustration of the blood oxygen saturation, the measurement curve 31 is disturbed by artifacts e.g. at 41–45 which appear with great amplitude and are correlated to the heart activities. A mere mean value formation of the measured value would therefore lead to false measurement results in many instances and, thus, to an incorrect control.

It is therefore inventively provided, first, that the measuring or sampling points lie at different times from heart cycle to heart cycle, so that the entire cycle is scanned over a plurality of heart cycles and the artifacts can be compensated for by component 5, FIG. 3, even given the employment of fewer measuring points in one cycle. During rest or for the case of a low load condition, measurement is not even undertaken in every heart cycle; and multiple measurements in every cycle are not undertaken until a very high load condition (where there is a relatively great dependency of the desired frequency on the change in the blood oxygen saturation). The minimum value is formed by component 5, FIG. 3, from a set of measured values such as obtained at measuring points 33, 34 and 35, 36. The great disturbances caused by the artifacts thereby drop out. As has been shown, artifacts always lead to an increase in the blood oxygen value when opto-electronic measuring probes are used. The minimum value is therefore a meaningful measurable variable for the actual load condition. The minimum value formation can also be followed by a means value formation which is known per se from U.S. Pat. No. 4,399,820.

The heat pacemaker can also function inhibited given this control system, i.e. to prevent stimulation of the heart by the stimulation frequency generator 16 given self-stimulation of the heart.

In exemplary operation of the control system of FIG. 3, values of $S_{O2max}$ and $S_{O2min}$ such as indicated in FIG. 2 at 51 and 52 may be entered as initial values into memory registers 7 and 8. Similarly, a value for $f_{min}$ may be programmed by supplying a selected value to input 16a of the component 16. In this way a value such as indicated at 53 in FIG. 2 may be entered in a receiving register of component 16, FIG. 3. A value for $\Delta f_{max}$ may also be entered by means of input 16a in a register of component 16, e.g. based on the span between lines 53 and 54 in FIG. 2. A value for $c_w$ may be introduced into a register of component 16 for example via an input 16b, FIG. 3. Accordingly, the values $f_{min}$ and $c_w$, for example, may be programmed by inserting selected values therefor into the $f_{min}$ and $c_w$ registers of component 16 via the inputs 16a and 16b.

With the patient initially in a condition of rest as represented at the extreme left in FIG. 4, sampling of the value of oxygen saturation may take place at times such as indicated at 33-36 in FIG. 5. In a first measurement cycle values of oxygen saturation as indicated at 63, 64, 65 and 66, FIG. 5, may be obtained at the output of signal amplifier 4, and a minimum value such as indicated at 63, FIG. 5, may be selected. By way of example, the signals from amplifier 4 may be sampled and converted to digital form in unit 5 and the successive digital values obtained during a measurement cycle may be stored in respective registers of component 5. At the end of each measurement cycle, the stored values are compared and the minimum value transmitted to the mean value forming unit 6. The unit 6 may then obtain an average value based on the outputs from component 5 which are supplied during a measurement interval, e.g. corresponding to several measurement cycles. Where a measurement cycle corresponds to eight heartbeat cycles (five such cycles being shown in FIG. 5), a measurement interval may correspond to sixteen heartbeat cycles, for example. The resultant measurement value stored in register 9 may be represented by a point such as 70 on curve 21 of FIG. 4. This measured value of oxygen saturation may also be stored in register 10 at the start of a time interval $\Delta t_2$. The interval $\Delta t_2$ may have a duration corresponding to ten or more measurement intervals. The value of oxygen saturation represented at point 70 in FIG. 4 and stored in memory 9, FIG. 3, gives rise to a value of $B_{S1}$ in a register of divider component 14, FIG. 3. In the embodiment of FIG. 6, the difference forming unit 12a has an input connected to the output of memory 8 instead of memory 7 which is possible since $S_{O2} - S_{O2}/S_{O2max} - S_{O2min}$ is the results of the expression:

$1 - B_{S1} = 1 - S_{O2max} - S_{O2}/S_{O2max} - S_{O2min}$ (the exponent of e), so that the value of $B_{S1}$ in divider 14a will correspond to the parenthetical expression, $$\frac{(S_{O2} - S_{O2min})}{(S_{O2max} - S_{O2min})},$$

which appears in the equation of FIG. 2. Component 16 may include an arithmetic processor for forming the product (designated as x hereafter) of the terms $-c_w$ and the square of such $B_{S1}$ value. The value of frequency then generated by component 16 will be represented by the expression $$f_p = f_{min} + \Delta f_{max}\, e^x \quad (1)$$

where $$x = -c_w \cdot \left(\frac{S_{O2} - S_{O2min}}{S_{O2max} - S_{O2min}}\right)^2 \quad (2)$$

Referring to FIG. 2, an operating point indicated at 71 on characteristic curve F may correspond with the value indicated at 70 in FIG. 4. Follower control during the interval represented at 21e on curve 21, FIG. 4, may be in the vicinity of point 71 on curve F. FIG. 2, and may be in conformity with equations (1) and (2) of this section of text, a large number of measurement intervals generating successive measurement values defining the portion 21e of curve 21.

At a time represented by point 73 on the $S_{O2}$ waveform 21, FIG. 4, the measurement value of $S_{O2}$ represented by point 70 may already have been transferred from memory 10 and processed by components 13 and 15, and a new value of $SO_2$ represented by point 73, FIG. 4, may be stored in both memory components 9 and 10.

As shown by control characteristics F, G and H, FIG. 2, the change in stimulation frequency for a given change in the measured value $S_{O2}$ is relatively small in the region of operation point 71, corresponding to relatively low stimulation frequencies, and is substantially greater in the region of operation point I corresponding to substantially higher stimulation frequencies. If $S_{O2min}$ in FIG. 2 is set at zero, and $S_{O2max}$ is set equal to one, it will be seen that the absciss a values for $S_{O2}$ in FIG. 2 will be numerically equal to the control values $B_{S1}$. In other words the curves F, G and H in FIG. 2 also represent the preferred non-linear control characteristic for relating each control value $B_{S1}$ in its range between $B_{S1}$ equals zero ($S_{O2} = S_{O2min}$) and $B_{S1}$ equals one ($S_{O2} = S_{O2max}$) to an appropriate respective value of stimulation frequency.

In contrast to the teachings of U.S. Pat. No. 4,399,820, for a given operating point on the control characteristic F, such as at I, a small change in the standardized control value $B_{S1}$ in successive measurement intervals produces a corresponding small change in stimulation frequency, while a larger change in the standardized control value $B_{S1}$ produces a correspondingly larger change in the stimulation frequency. Thus each different degree of change of the standardized control value produces a respective different degree of change in the stimulation frequency.

The disclosure including the drawings of Wirtzfeld U.S. Pat. No. 4,399,820 issued Aug. 23, 1983 is incorporated herein by reference for its showing of an implanted heart pacemaker and catheter system to which the control system and method of the present invention are applicable, and for its teaching of details concerning sensor means including the measurement probe, and the probe and error compensation circuitry, for obtaining compensated measurement signals which are a function of a physiological parameter related to a patient's blood circulation requirements, preferably the central venous oxygen saturation. This U.S. Pat. No. 4,399,820 and Wirtzfeld et al U.S. Pat. No. 4,202,339 of May, 1980 are further incorporated herein by reference in their entireties by way of background.

By way of example, component 17 may store a value of $B_{S2}$ obtained based on the difference ($\Delta S_{O2}$) between the value of $S_{O2}$ corresponding to point 70 and the value $S_{O2min}$ from memory 8, divided by $\Delta S_{O2max}$ from component 11. This value for point 70 may then be compared with the corresponding $B_{S2}$ value for point 73. If the difference, $\Delta B_{S2}$, had a magnitude less than the absolute value of $A_2$, i.e. was algebraically less than the $+A_2$ value and greater than the $-A_2$ value, then comparator 17 would signal generator component 16 to superimpose a fixed frequency increment $\Delta f_{opt}$ on the value of generator frequency simultaneously produced by the follower control in response to the current $B_{S1}$ value from component 14. As shown by level 74 of curve 22, however, the magnitude of $\Delta B_{s2}$ exceeds the absolute value of $A_2$, indicating a relatively substantial change in $B_{S2}$ during this optimizing interval ($\Delta t_2$) between points 70 and 73, FIG. 4. Later in load phase L2, FIG. 4, between points 75 and 76 on $S_{O2}$ curve 21, the change in the optimizing criterion $B_{S2}$ is within the range between $+A_2$ and $-A_2$, as indicated by level 77 of waveform 22, and comparator 17 produces a frequency increment as indicated at 20-1; this frequency increment $\Delta f_{opt}$ may correspond to that indicated at step a shown in FIG. 2. At the time corresponding to point 76 on curve 21, a value for the control variable $B_{S1}$ is read from component 14 into the generator 16, so that the resultant stimulation frequency $f_p$ is based on simultaneous contributions from the follower control including component 14 and the optimizing control including components 15 and 17. The new operating point might correspond to point 80 in FIG. 2.

At a time corresponding to point 81 on $S_{O2}$ curve 21, the comparator 17 obtains a further value of $\Delta B_{S2}$ and determines that the change between points 76 and 81 has been favorable. Accordingly, the optimizing frequency change at 20-1 is retained, while the proportional control simultaneously introduces a new frequency corresponding to an operating point such as indicated 82, FIG. 2. (The measurement values obtained by the measurement means 3, 4, 5, 6, FIG. 3, in the time interval between points 80 and 82 in FIG. 2, would be plotted on a curve offset from curve F by the distance of step a since the frequency increment $\Delta f_{opt}$ is added to the frequency value corresponding to these measurement values based on curve F.)

In the region of curve 21 between points 84 and 85, the change in $B_{S2}$ is less than $+A_2$ as indicated by level 86 so that frequency increment $\Delta f_{opt}$ is introduced as indicated at 20-2. The change in $B_{S2}$ in the optimizing time interval $\Delta t_2$ between points 85 and 87 on curve 21, however, is greater than the absolute value of $A_2$ and in a direction indicating that the frequency increment at 20-2 is to be cancelled by an opposite frequency increment at 20-3.

In a mode of operation of comparator 17 which is analogous to operation shown in the eleventh figure of U.S. Pat. No. 4,399,820, a value of $\Delta B_{S2}$ at 86' which is algebraically greater than $-A_2$ and less than $+A_2$ can produce a frequency change at 20-2 after a time delay of $\Delta t_2$. (The interval $\Delta t_2$ in FIG. 4 would then be analogous to the time interval in the U.S. patent relating to a change in time t sub five, $\Delta t_5$, as well as to a change in time t sub four, $\Delta t_4$.) By way of example, the value of $\Delta B_{S2}$ at level 88, FIG. 4, is less than $+A_2$, indicating that the load has not substantially decreased; accordingly, the optimizing frequency change $+\Delta f_{opt}$ at 20-2 is cancelled as indicated at 20-3. For simplicity comparator circuit 17 may only introduce and selectively retain or cancel positive changes, $+\Delta f_{opt}$, and not utilize the further procedure of initiating and selectively retaining changes of negative polarity (such as are also utilized in U.S. Pat. No. 4,399,820 e.g. according to claims three, four and five thereof).

It will be apparent that many modifications and variations may be made without departing from the scope of the teachings and concepts of the present invention.

We claim as our invention:

1. A control system for matching the stimulation frequency of a heart pacemaker to the load condition of a patient, said system comprising:

controllable means for stimulating said patient's heart with stimulation pulses supplied thereto at said stimulation frequency;

means for obtaining in successive intervals measurement values representing the momentary central venous blood oxygen saturation in said patient's heart;

means for forming and storing a maximum signal corresponding to a maximum blood oxygen saturation occurring during a selected time consisting of a plurality of successive intervals;

means for forming and storing a minimum signal corresponding to a minimum blood oxygen saturation occurring during said selected time;

means for forming and storing a current signal corresponding to the blood oxygen saturation during a current one of said intervals;

means for forming a first difference signal which is the difference between said maximum signal and said minimum signal;

means for forming a second difference signal which is the difference between a selected one of said maximum signal or said minimum signal and said current signal; and means for generating a control signal for controlling said means for stimulating said patient's heart, said control signal including a factor which is the ratio of said first and second difference signals, said means for stimulating changing the stimulation frequency in a direction and magnitude as a function respectively of the sign and the magnitude of said ratio.

2. A control system as claimed in claim 1 further comprising means for generating an optimizing control signal supplied simultaneously with said control signal to said means for stimulating said patient's heart, and means for disabling said means for generating said optimizing control signal if a change in the blood oxygen saturation of said patient within a selected time following said optimizing control signal exceeds a selected limit.

3. A control system as claimed in claim 2 wherein said means for generating said optimizing control signal comprises:
    means for storing a preceding signal corresponding to the blood oxygen saturation during an interval preceding said current one of said intervals;
    means for forming a third difference signal which is the difference between said maximum signal and said preceding signal; and
    means for dividing said first and third difference signals, the result of said division being said optimizing control signal.

4. A control system as claimed in claim 2 wherein said means for disabling said means for generating said optimizing control signal is a comparator connected between said means for generating said optimizing control signal and said means for stimulation said patient's heart, said comparator having selected upper and lower limits and comparing said optimizing control signal to said limits, and said comparator forwarding said optimizing control signal to said means for stimulating only if said optimizing control signal exceeds said limits.

5. A control system as claimed in claim 2 wherein said means for stimulating said patient's heart includes means for setting a selected minimum stimulation frequency $f_{min}$, means for setting a constant $c_w$, and means for setting a selected maximum frequency difference $f_{max}$, and wherein said means for stimulating said patients heart generates successive stimulation frequency values $f_p$ based simultaneously on said control signal and said optimizing control signal according to the relationship $$f_p = f_{min} + \alpha f_{max} \exp(=c_w B_{S1}^2) + \Delta f_{opt},$$

wherein $B_{S1}$ is said factor, and $\Delta f_{opt}$ is said optimizing control signal.

6. A control system as claimed in claim 1 wherein said means for obtaining measurement values includes means for varying the chronological position of said successive intervals with respect to the heartbeat of said patient.

7. A control system as claimed in claim 6 wherein said means for obtaining measurement values is further defined by means for obtaining measurement values in successive intervals between successive heartbeats of said patient.

8. A control system as claimed in claim 7 wherein said means for varying is a means for shifting the phases of the successive intervals following each hearbeat of said patient relative to the intervals preceding said heartbeat.

9. A method for matching the stimulation frequency of a heart pacemaker to the load condition of a patient, said method comprising the steps of:
    stimulating said patient's heart with stimulation pulses supplied thereto at said stimulation frequency;
    obtaining in successive intervals measurement values representing the momentary central venous blood oxygen saturation in said patient's heart;
    forming and storing a maximum signal corresponding to a maximum blood oxygen saturation occurring during said selected time consisting of a plurality of successive intervals;
    forming and storing a minimum signal corresponding to a minimum blood oxygen saturation occurring during said selected time;
    forming and storing a current signal corresponding to the blood oxygen saturation during a current one of said intervals;
    forming a first difference signal which is the difference between said maximum signal and said minimum signal;
    forming a second difference signal which is the difference between a selected one of said maximum signal or said minimum signal and said current signal;
    generating a control signal for controlling stimulation of said patient's heart, including generating a factor in said control signal which is the ratio of said first and second difference signals; and
    changing the stimulation frequency in a direction and magnitude as a function respectively of the sign and the magnitude of said ratio.

10. A method as claimed in claim 9 further comprising the steps of:
    generating an optimizing control signal; and
    controlling stimulation of said patient's heart using said optimizing control signal simultaneously with said control signal.

11. A method as claimed in claim 10 comprising the additional steps of:
    monitoring the change, if any, in the blood oxygen saturation of said patient within a selected time following generating said optimizing control signal; and
    disabling generating of said optimizing control signal if the change in blood oxygen saturation within said selected time exceeds a selected limit.

12. A method as claimed in claim 10 wherein the step of generating said optimizing control signal comprises the steps of:
    storing a preceding signal corresponding to the blood oxygen saturation during an interval preceding said current one of said intervals;
    forming a third difference signal which is the difference between said maximum signal and said preceding signal; and
    dividing said first and third difference signals, the result of said division being said optimizing control signal.

13. A method as claimed in claim 10 comprising the additional steps of:
    selecting a minimum stimulation frequency $f_{min}$;
    selecting a constant $c_w$;
    selecting a maximum frequency difference $\Delta f_{max}$, and wherein the step of controlling stimulating of said patient's heart is further defined by generating successive stimulation frequency values $f_p$ based simultaneously on said control signal and said optimizing control signal according to the relationship $$f_p = f_{min} + \alpha f_{max} \exp(=c_w B_{S1}^2) + \Delta f_{opt},$$

wherein $B_{S1}$ is said factor, and $\Delta f_{opt}$ is said optimizing control signal.

14. A method as claimed in claim 9 wherein the step of obtaining measurement values includes the step of varying the chronological position of said successive intervals with respect to the heartbeat of said patient.

15. A method as claimed in claim 14 wherein the step of obtaining measurement values is further defined by obtaining measurement values in successive intervals between successive heartbeats of said patient.

16. A method as claim in claim 15 wherein the step of varying the chronological position of said successive intervals is further defined by shifting the phases of the successive intervals following each heartbeat of said patient relative to the intervals preceding said heartbeat.

* * * * *

UNITED STATES PATENT AND TRADEMARK OFFICE
CERTIFICATE OF CORRECTION

PATENT NO. : 4,870,968
DATED : October 3, 1989
INVENTOR(S) : Wirtzfeld, et al

It is certified that error appears in the above—identified patent and that said Letters Patent is hereby corrected as shown below:

Under title page please cancel:

UNITED STATES PATENT [19]
        "Wiertzfeld" et al.

and substitute:   UNITED STATES PATENT [19]
        --Wirtzfeld-- et al.

Also please cancel: [75] Inventors: Alexander "Wiertzfeld"

and substitute:   [75] Inventors: Alexander --Wirtzfeld-- therefor.

Signed and Sealed this

Second Day of July, 1991

Attest:

HARRY F. MANBECK, JR.

Attesting Officer        Commissioner of Patents and Trademarks